United States Patent
Barnes et al.

(10) Patent No.: US 10,107,819 B2
(45) Date of Patent: Oct. 23, 2018

(54) FOOD ALLERGEN DETECTION METHODS AND SYSTEMS USING MOLECULARLY IMPRINTED POLYMERS

(71) Applicant: ALLERGY AMULET, INC., Madison, WI (US)

(72) Inventors: Abigail Barnes, Madison, WI (US); Joseph BelBruno, Hanover, NH (US)

(73) Assignee: ALLERGY AMULET, INC., Madison, WI (US)

( * ) Notice: Subject to any disclaimer, the term of this patent is extended or adjusted under 35 U.S.C. 154(b) by 224 days.

(21) Appl. No.: 14/908,514

(22) PCT Filed: Jul. 29, 2014

(86) PCT No.: PCT/US2014/048676
§ 371 (c)(1),
(2) Date: Jan. 28, 2016

(87) PCT Pub. No.: WO2015/017442
PCT Pub. Date: Feb. 5, 2015

(65) Prior Publication Data
US 2016/0209420 A1    Jul. 21, 2016

Related U.S. Application Data

(60) Provisional application No. 61/859,556, filed on Jul. 29, 2013.

(51) Int. Cl.
*G01N 33/68* (2006.01)
*G01N 21/78* (2006.01)
(Continued)

(52) U.S. Cl.
CPC ............ *G01N 33/68* (2013.01); *G01N 21/78* (2013.01); *G01N 33/54306* (2013.01);
(Continued)

(58) Field of Classification Search
CPC ....... G01N 2021/752; G01N 2021/757; G01N 21/77; G01N 21/78; G01N 2333/415;
(Continued)

(56) References Cited

U.S. PATENT DOCUMENTS 6,461,873 B1    10/2002 Catania et al.
6,818,181 B2 *  11/2004 Lee .................. G01N 33/543
                                                422/412
(Continued)

FOREIGN PATENT DOCUMENTS

EP    0 376 135        7/1990
WO    2004-020655  *   3/2004
(Continued)

OTHER PUBLICATIONS

Li et al. Talanta, vol. 99, Jul. 22, 2012, pp. 811-815.*
(Continued)

*Primary Examiner* — Maureen Wallenhorst
(74) *Attorney, Agent, or Firm* — Foley & Lardner LLP

(57) ABSTRACT

Methods and devices for the detection of food allergens using molecularly imprinted polymers that are imprinted for a target food allergen. A molecularly imprinted polymer may be imprinted using surface imprinting or other procedures. Detection of food allergens, such as peanut allergens, may be accomplished using all or a portion of a protein food allergen as a template to produce a molecularly imprinted polymer for food allergen detection. A portion utilized can be one that creates receptor sites in the molecularly imprinted polymer that are unique or more unique to the target food allergen than receptor sites that would be created if an entire food allergen molecule were utilized.

16 Claims, 4 Drawing Sheets

(51) Int. Cl.
    *G01N 33/02* (2006.01)
    *G01N 33/04* (2006.01)
    *G01N 33/12* (2006.01)
    *G01N 33/14* (2006.01)
    *G01N 33/543* (2006.01)
    *G01N 21/75* (2006.01)

(52) U.S. Cl.
    CPC ........... *G01N 33/02* (2013.01); *G01N 33/025* (2013.01); *G01N 33/04* (2013.01); *G01N 33/12* (2013.01); *G01N 33/14* (2013.01); *G01N 2021/752* (2013.01); *G01N 2021/757* (2013.01); *G01N 2333/415* (2013.01); *G01N 2600/00* (2013.01); *G01N 2800/24* (2013.01)

(58) Field of Classification Search
    CPC ......... G01N 2800/24; G01N 33/54306; G01N 33/68; G01N 33/02; G01N 33/025; G01N 33/04; G01N 33/08; G01N 33/12; G01N 33/14
    USPC ......... 436/20, 21, 22, 23, 86, 149, 164, 165; 422/400, 401, 418, 419, 430, 68.1, 82.01, 422/82.02; 435/7.1
    See application file for complete search history.

(56) References Cited

U.S. PATENT DOCUMENTS

| | | | |
|---|---|---|---|
| 7,829,843 | B2 | 11/2010 | Burnin et al. |
| 2009/0110601 | A1* | 4/2009 | Levi ................. C01N 33/54386 422/68.1 |
| 2010/0039124 | A1 | 2/2010 | Belbruno et al. |
| 2013/0040399 | A1 | 2/2013 | Belbruno et al. |
| 2014/0227795 | A1 | 8/2014 | Belbruno |
| 2014/0242237 | A1 | 8/2014 | Belbruno et al. |
| 2014/0295406 | A1 | 10/2014 | Sundvor et al. |

FOREIGN PATENT DOCUMENTS

| | | |
|---|---|---|
| WO | WO-2006/016986 A2 | 2/2006 |
| WO | WO-2008/045596 A2 | 4/2008 |
| WO | WO-2012/034115 A1 | 3/2012 |
| WO | WO-2012/040540 A1 | 3/2012 |
| WO | WO-2013/033383 A2 | 3/2013 |
| WO | WO-2013/033541 A1 | 3/2013 |
| WO | WO-2013/188675 A1 | 12/2013 |
| WO | WO-2015/017442 A2 | 2/2015 |
| WO | WO-2015/066027 A2 | 5/2015 |
| WO | WO-2016/149253 A1 | 9/2016 |

OTHER PUBLICATIONS

Sontimuang et al. Analytical Biochemistry, vol. 410, Dec. 2, 2010, pp. 224-233.*
First Examination Report in Australian Application No. 2014296379, dated Sep. 25, 2017 (4 pages).
International Search Report & Written Opinion in International Application No. PCT/US2014/048676, dated Mar. 16, 2015 (16 pages).
Latif et al., "Amino acid composition, antinutrients and allergens in the peanut protein fraction obtained by an aqueous enzymatic process," Food Chemistry 136(2013): 213-217.
Pomes et al., "Peanut allergen (Ara h 1) detection in foods containing chocolate," Journal of Food Protection 67(4): 793-798, 2004.

* cited by examiner

FOOD ALLERGEN DETECTION METHODS AND SYSTEMS USING MOLECULARLY IMPRINTED POLYMERS

RELATED APPLICATION DATA

This application claims the benefit of priority of U.S. Provisional Patent Application Ser. No. 61/859,556, filed on Jul. 29, 2013, and titled "Molecularly Imprinted Polymers for Detecting Allergens and Point-of-Consumption Detection Device," which is incorporated by reference herein in its entirety.

FIELD OF INVENTION

The present invention generally relates to the field of food allergen detection. In particular, the present invention is directed to food allergen detection methods and systems using molecularly imprinted polymers.

BACKGROUND

Many people suffer from allergies to foods of various types. While the severity of allergic reactions varies, many reactions can be fatal. Preventing the inadvertent ingestion of and/or exposure to food allergens is a concern for many. Present allergen-detection tools for assisting individuals with avoiding exposure generally require sophisticated technology and expertise. These tools are also typically too bulky for individuals to use at the point of consumption of food.

SUMMARY OF THE DISCLOSURE

In one implementation, a method for detecting a food allergen at the point of consumption of a food item by a first mammal is provided. The method includes exposing a first target item with a portable food allergen detection platform at the point of consumption, the portable food allergen detection platform including; a substrate; and a molecularly imprinted polymer layer in contact with the substrate, the molecularly imprinted polymer layer including a polymer imprinted on a first surface of the polymer with receptor sites created by a first template, the receptor sites keyed to detect a first indicator of a first food allergen; detecting the presence or absence of one or more molecules of the first indicator bound to one or more of the receptor sites; and providing a visual indication of the presence of the first food allergen.

In another implementation, a method for detecting a food allergen at the point of consumption of a food item by a first mammal is provided. The method includes exposing a first target item with a portable food allergen detection platform at the point of consumption, the portable food allergen detection platform including: a substrate; and a molecularly imprinted polymer layer in contact with the substrate, the molecularly imprinted polymer layer including a polymer imprinted with receptor sites created by a first template, the receptor sites keyed to detect a first indicator of a first food allergen; providing contact of a color development agent with one or more molecules of the first indicator bound to one or more of the receptor sites; detecting a color change in the color development agent to provide a visual indication of the presence of the first food allergen to the first mammal.

In yet another implementation, a method of manufacturing a food allergen detection device is provided. The method includes depositing a template of a first food allergen on a first surface of a first substrate, the template being a selected portion of a protein associated with the first food allergen, the selected portion including a segment of the protein unique to the protein; depositing a pre-polymerization solution on a second surface of a second substrate, the pre-polymerization solution including a functional monomer and a crosslinking agent; contacting the first surface with the second surface to stamp the template onto the pre-polymerization solution; initiating polymerization of the template and the pre-polymerization solution; and removing the template and any non-polymerized portions of the pre-polymerization solution to form a molecularly imprinted polymer having receptor sites keyed for the selected portion of the protein.

In yet another implementation, a food allergen detection device for detecting a food allergen at the point of consumption of a food item by a first mammal is provided. The device includes a holder; a portable food allergen detection platform removably within the holder, the portable food allergen detection platform including: a substrate; and a molecularly imprinted polymer layer in contact with the substrate, the molecularly imprinted polymer layer including a polymer imprinted on a first surface of the polymer with receptor sites created by a first template, the receptor sites keyed to detect a first indicator of a first food allergen; and a color development agent, the color development agent selected and configured to provide a visual indication of the presence of the first food allergen upon detecting a binding of one or more molecules of the first indicator to one or more of the receptor sites.

In still yet another implementation, a method for detecting a food allergen, the method comprising: exposing a first target item with a molecularly imprinted polymer layer having a polymer imprinted with receptor sites created by a first template, the receptor sites keyed to a first food allergen; detecting the presence or absence of the first food allergen in the first target item, the detecting including observing a visual indication or electrical signal indicating the presence or absence of the food allergen.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Molecularly imprinted polymers (MIPs) can be utilized in systems and methods for detecting the presence of food allergens. Food allergens vary in form, chemical makeup, and location within substances consumed by humans. Example consumable substances that may include a food allergen include, but are not limited to, an animal product, a grain (e.g., gluten), a vegetable, a fruit, a dairy product, a fish, a beverage, a legume (e.g., peanut), a chocolate, a synthetic food chemical (e.g., monosodium glutamate (MSG), and any combinations thereof. A consumable substance may include one or more food allergens. In one example, a food allergen may include a food protein. Due to the importance of peanut allergies, a peanut-related food allergen is used in an exemplary fashion in this disclosure. It is contemplated that other food allergens may replace the discussed peanut-related food allergen in the example, embodiment, implementation or other aspect of the disclosure. One way to test for the presence of a peanut-related food allergen is to test for a peanut protein allergen. Examples of a peanut protein include, but are not limited to, *arachis hypogaea* allergen 1 (ara h1), *arachis hypogaea* allergen 2 (ara h2), *arachis hypogaea* allergen 3 (ara h3), and any combination thereof.

A food allergen may be present in any of a variety of items that may be a target for detecting a food allergen. For example, a food allergen target item may be a food itself (or a portion thereof) or an item that the food has come into contact with (e.g., a serving utensil, a table, etc.). Food allergen target items may come in a variety of forms including, but not limited to, a solid, a liquid, a gas, a suspension, and any combinations thereof. Example solid food allergen target items include, but are not limited to, a solid food (e.g., a bread, a nut), a plate, a table, a utensil, and any combinations thereof. Example liquid food allergen target items include, but are not limited to, a liquid food, a beverage (e.g., a soda, milk, a juice), a food extract, and any combinations thereof. Examples of a suspension food allergen target item include, but are not limited to, an allergen suspended in air (e.g., a food allergen in particulate form), an allergen suspended in water, and any combinations thereof Humans are used herein in an exemplary fashion when discussing food allergens. It is intended that the embodiments, implementation, examples and other aspects of the present disclosure apply to humans and other mammals.

Figure 1:
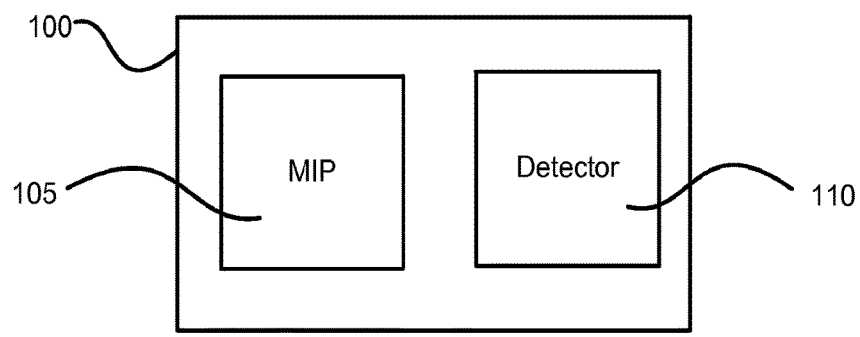
FIG. 1 illustrates one exemplary implementation of a food allergen detection device.

FIG. 1 illustrates an exemplary implementation of a food allergen detection device 100. Food allergen detection device 100 includes a molecularly imprinted polymer (MIP) 105 that is coded/keyed to allow the binding of a target food allergen (e.g., a peanut protein allergen) to MIP 105. Food allergen detection device 100 also includes a detector element 110 that is configured to detect the binding of the target food allergen to allow the indication of the presence and/or absence of the target food allergen with respect to a target item.

Figure 2:
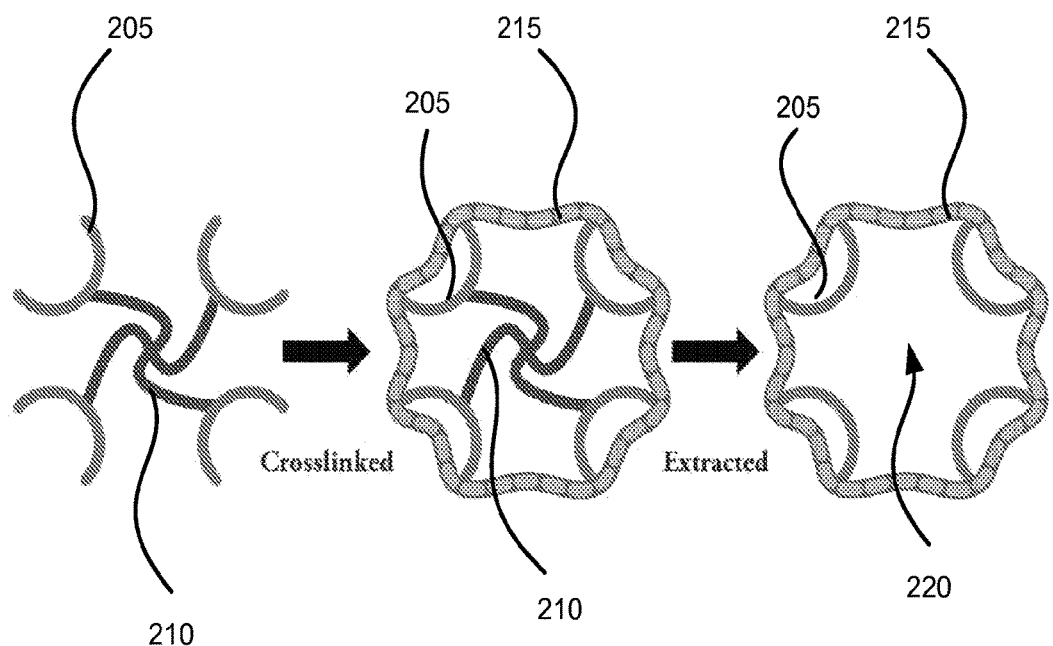
FIG. 2 illustrates one exemplary implementation of a generalized process of an MIP production.

A molecularly imprinted polymer, such as MIP 105 and other MIP's discussed herein, may be produced by any of a variety of methods. FIG. 2 illustrates one example of a generalized process of an MIP production. Host molecules 205 (functional monomers/polymers) are shown bound to a template 210. A template (e.g. template 210) is a molecule that resembles closely a target food allergen (e.g., a molecule of the food allergen itself, a portion of a molecule of the food allergen, etc.). Host molecules 205 are crosslinked 215 to form a polymer with template 210 in place. Template 210 is then removed to form a molecularly imprinted polymer having a cavity 220 that provides a receptor site for binding of the target food allergen.

Example polymers include, but are not limited to, poly (4-vinylphenol) (PVP), poly(urethane) (PU), poly(methyl-methacrylate) (PMMA), poly(methacrylic acid), and any combination thereof.

A template molecule may bind to a host molecule in a variety of ways. Example ways of binding a template molecule to a host molecule include, but are not limited to, a covalent binding, an ionic binding, a hydrogen bond binding, and any combinations thereof. Extraction of a template may be done using any procedure that allows the specific template to be removed while leaving the MIP having the cavity/receptor sites intact. Selection of a template removal procedure may include consideration of the strength of the binding of the template to the host molecule (e.g., the stronger the binding, the more difficult the removal). The strength of the binding of a host molecule and a template may also impact selection of the host molecule to allow for a desired level of binding of the template to the host molecule for a given target food allergen. Example ways of extracting a template include, but are not limited to, chemical washing, water washing, and any combinations thereof.

A template for coding/keying an MIP may include one or more target food allergen molecules. Multiple food allergens are discussed above. In one such example, a template is a food allergen molecule. In another such example, a template is a food protein molecule. In still another such example, a template is a peanut protein. In yet another such example, a template is an ara h1 peanut protein.

A template for coding/keying an MIP may also include only a portion of one or more target food allergen molecules. A portion of a target food allergen molecule may provide a more unique keying in the creation of a more specific receptor site in the MIP that is more unique to the target food allergen. In using an entire food allergen molecule (e.g., the component of a food that causes an allergic reaction in a human) it is possible that a cavity/receptor site created in an MIP may allow binding of a molecule that is similar in shape, size, and/or binding characteristics to a target food allergen but that is not the target food allergen. In such an example, food allergen detection may have the potential for a false positive. In one exemplary aspect using a portion of a food allergen molecule, which is more unique to the target food allergen (e.g., in binding characteristics to the host molecule), as a template may increase the specificity of the resulting MIP receptor sites for binding to the target food allergen. In one example, a template is a portion of a food allergen molecule. A portion utilized may be one that creates receptor sites in the molecularly imprinted polymer that are unique or more unique (i.e., are more specifically keyed) to the target food allergen than receptor sites that would be created if an entire food allergen molecule were utilized. One exemplary benefit of such increased targeting may be the minimization of false positives and/or false negatives in detecting a target food allergen. In another example, a template is a portion of a food protein molecule. In still another example, a template is a portion of a peanut protein. In yet another example, a template is a portion of an ara h1 peanut protein. In still yet another example, a template is a protein epitope. In a further example, a template is a 14-peptide epitope (sequence: DLAFPGSGEQVEKL), for ara h1.

Figure 3:
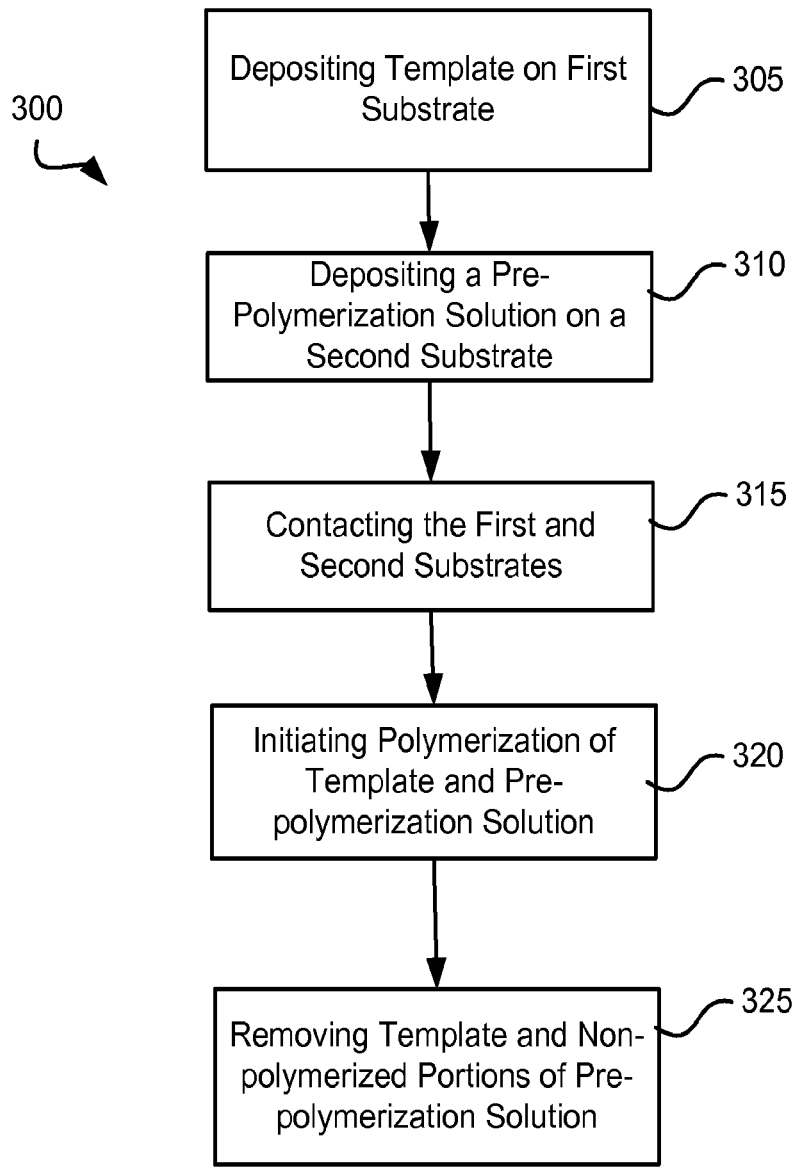
FIG. 3 illustrates one exemplary implementation of a method of surface imprinting an MIP.

One example method of making an MIP includes using surface imprinting of a template onto a polymer. A surface imprinted MIP includes surface receptor sites that larger target allergens, such as food proteins, can have access to potentially more easily than internal cavities of a polymer matrix. In one example, a surface imprinted MIP is in the form of a thin film. Any of the implementations of a method of detecting a food allergen and/or devices for detecting a food allergen of the present disclosure may include a surface imprinted MIP. FIG. 3 illustrates one example of a method of surface imprinting an MIP. At step 305, a template is deposited on a surface of a first substrate. Example templates are discussed above. In one example, a monomeric protein template is utilized for a target allergen that exists in nature, at least in some instances, as a trimeric protein. In one such example, an ara h1 protein may exist in nature as a trimer and a monomer of the protein may be used as a template. In another example, a template is a 14-peptide epitope (sequence: DLAFPGSGEQVEKL), for ara h1. A coating may be applied to the first substrate. In one example, a poly(dimethylsiloxane) (PDMS) coating is applied to the first substrate and the template is applied thereto. In one such example, PDMS is solubilized and spin coated on the surface of the first substrate.

At step 310, a pre-polymerization solution is deposited on a surface of a second substrate. Example substrates include, but are not limited to, a quartz, a glass, alumina, mica, silicon, a III-IV semiconductor compound, a plastic, a paper, and any combinations thereof. A substrate may have a variety of properties. Example properties of a substrate include, but are not limited to, inclusion of a rigid material, inclusion of a flexible material, being a monolithic structure, being a multilayer structure, being a composite structure, and any combinations thereof. In one example, a substrate includes a flexible material. In another example, a substrate includes a rigid material. In another example, a substrate is a multilayer or other composite structure having constituents of different properties and compositions. A substrate may also include one or more additional electronic elements integrated into the substrate. Example additional electronic elements include, but are not limited to, a thermistor, an integrated circuit element, and any combinations thereof. A pre-polymerization solution includes the components for building the MIP with the template. Example components for a pre-polymerization solution include, but are not limited to, a functional host molecule (e.g., a functional monomer, a functional polymer), a crosslinking agent, a solvent, a polymerization initiator, and any combinations thereof. A functional host molecule is a molecule (such as host molecule 205) used to build the polymer of an MIP. Example polymers for a surface imprinted MIP include, but are not limited to, poly(4-vinylphenol) (PVP), poly(urethane) (PU), poly(methylmethacrylate) (PMMA), poly(methacrylic acid), and any combination thereof. In one example, a pre-polymerization solution includes a functional host molecule and a crosslinking agent. In another example, a pre-polymerization solution includes a functional host molecule, a crosslinking agent, a solvent, and a polymerization initiator. Ratios of components in a pre-polymerization solution are such that polymerization of the components and the binding of the template can occur. In one example, a ratio of crosslinking agent to functional host is about 1:1 to about 10:1. In another example, a ratio of crosslinking agent to functional host is 1:1 to 10:1. In yet another example, a ratio of crosslinking agent to functional host is about 1:1. In still another example, a ratio of crosslinking agent to functional host is 1:1. In still yet another example, a ratio of crosslinking agent to functional host is about 2:1. In a further example, a ratio of crosslinking agent to functional host is 2:1.

At step 315, the surfaces of the first and second substrates having the template and the pre-polymerization solution are contacted to stamp the template to the pre-polymerization solution. At step 320, polymerization is initiated. Example ways to initiate polymerization include, but are not limited to, a photochemical initiation, an application of heat, a catalyst, and any combinations thereof. In one example, polymerization is initiated by the application of light.

At step 325, after the polymerization is complete, the template and non-polymerized portions of the pre-polymerization solution (e.g., remaining non-polymerized host molecules, crosslinking agent, solvent, polymerization initiator) are removed. Example ways to remove a template are discussed above. In one example, a template and non-polymerized portions of a pre-polymerization solution are washed for removal. After a template and non-polymerized portions of a pre-polymerization solution are removed, the resulting MIP can be utilized to detect the selected target food allergen.

In another example of a method of surface imprinting an MIP, a food allergen protein template stamp is produced using glass slides as substrates. The glass slides are cleaned in a piranha solution, rinsed with water, and stored under inert atmosphere. The protein template self assembles on a PDMS coating that is spin coated onto a surface of one of the glass slides to produce the protein template stamp. A degassed pre-polymerization gel-point solution including a functional monomer, a crosslinking agent, a solvent, and a polymerization initiator is deposited on a surface of a second of the glass slides. The protein template stamp is pressed onto the pre-polymerization solution. Polymerization is initiated photochemically and/or thermally. After the polymerization is complete, the first glass slide is removed and the second glass slide is washed repeatedly to remove the protein and non-polymerized portions of the pre-polymerization solution. Removal of a template can be confirmed by analysis of a wash solution using uv/vis spectroscopy. After washing, the resulting MIP is ready to be utilized for detection of a target food allergen protein.

Other surface imprinting methods for making an MIP for food allergen detection may also be utilized. Additionally, alternative methods to surface imprinting may be utilized to make an MIP for detection of a food allergen in any of the methods and devices disclosed herein. One alternative example includes using a hydrogel process for producing a hydrogel MIP. In one such example, a functional host, a template, a polymerization initiator, and a crosslinking agent are directly mixed. In one example, the ratio of functional host to crosslinking agent is 1:1. Example polymer hosts for a hydrogel implementation include, but are not limited to poly(hydroxyethylmethacrylate) (PHEMA), poly(vinylpyrrolidone) (PVP), and any combination thereof.

Other example methods for making an MIP that are alternatives to the surface imprinting discussed above include examples where the template and host molecules are mixed together to form a polymer matrix. In one such example, an MIP film is produced using a phase inversion-spin coating onto a suitable substrate. Examples of wet phase inversion procedures can be found in Wang, et al. (1997) *Langmuir* 13:5396; Shibata, et al. (1999) *J. Appl. Poly. Sci.* 75:1546; Trotta, et al. (2002) *J. Membr. Sci.* 201:77, Crabb, et al. (2002) *J. Appl. Polym. Sci.* 86:3611; Richter, et al. (2006), *J. Appl. Polym. Sci.* 101:2919; Campell, et al. (2009) *Surface and Interface Analysis* 41:347), each of which is incorporated herein by reference for the methods of production of MIP disclosed therein. In one such example, host molecules are dissolved with a template in a theta solvent. A template-host network is allowed to form in solution and precipitated by immersion in a non-solvent. In a specific example, a thin film MIP having a PVP polymer can be produced by mixing PVP host molecules in a conventional casting solution with a template in a suitable solvent (e.g., methanol, dimethylformamide (DMF), etc.). The solution is allowed to mix at room temperature (e.g., from six to 24 hours) to form a hydrogen-bonded network in solution. Subsequently, thin films are cast onto a substrate using a spin coater (e.g., at 5000-7000 rpms for about 30 seconds). The thin film is allowed to dry and the template molecule is removed by washing (e.g., with water).

An MIP may be in the form of a thin film. A thin film may be of a variety of thicknesses. In one example, a thin film MIP has a thickness of about 300 nanometers (nm) to about 5 micrometers. In another example, a thin film MIP has a thickness of 300 nm to 5 micrometers.

Returning to FIG. 1, MIP 105 may be included in device 100 as part of a food allergen detection platform. A food allergen detection platform may include a substrate and an MIP layer. Examples of a substrate include, but are not limited to, a glass, a plastic, a paper, a polymer, and any combinations thereof. In one example, a food allergen detection platform is in the form of a test strip. As discussed above, an MIP may be formed on a substrate (e.g., via surface imprinting, stamping). In another example, an MIP may be applied to a substrate after it is formed (e.g., via spin coating or other application technique). An MIP layer may be of any thickness that allows for the desired detection of a target food allergen. The MIP layer may be of a variety of forms. Example forms for an MIP layer include, but are not limited to, a thin film, a membrane, a nanowire, micromonolith, and any combinations thereof. In one example, an MIP layer is a thin film.

Detector 110 may include any detector capable of determining the presence and/or absence of a target food allergen that binds to one or more of the receptor sites of MIP 105. Detection of a presence of a target food allergen may include detection of an amount of a target food allergen that is present. Detection may also include determination of binary indication that the target food allergen is present or not present. Detection of a presence and/or absence of a target food allergen may include the detection of the food allergen itself or an indicator of the presence of the food allergen. In one example, an indicator of the presence of the food allergen may be a molecule or portion of a molecule of a target food allergen. A detector may be included in a food allergen detection device in a variety of ways. Example ways of inclusion include, but are not limited to, as a component of a food allergen detection platform, as a component of an MIP, as a component separate from a food allergen detection platform, as a component separate from an MIP, and any combinations thereof.

A variety of detectors can be used. In one example, a detector that provides a visual indication of the presence of food allergen bound to one or more receptor sites is utilized. In one such example, a detector includes a color development agent. A color development agent is an agent that changes color in the presence of a target food allergen bound to one or more of the receptor sites of an MIP. Example color development agents include, but are not limited to, Coomassie Brilliant Blue (CBB). In one example, a color development agent is Coomassie Brilliant Blue. A visual indicator may have different degrees of visual indication depending on the quantitative amount of a target food allergen that is bound to one or more receptor sites of an MIP. Different degrees of visual indication may provide a user of a detection device (such as device 100) with an ability to discern the level of a food allergen present. In one such example, a color development agent can have different colors (and/or different degrees of color) based on the amount of a target food allergen bound to one or more receptor sites of an MIP. In another example, a visual indicator is configured to provide a visual indication when the amount of a target food allergen bound to one or more receptor sites of an MIP reaches a level that is capable of eliciting an allergic reaction in an allergy sufferer. The amount of a food allergen that can cause an allergic reaction differs from one target food allergen to another and example amounts for a specified target food allergen can be readily determined.

A target food allergen may bind to a receptor site of an MIP in a variety of ways. Example ways of binding a food allergen to a receptor site of an MIP include, but are not limited to, a covalent binding, an ionic binding, a hydrogen bond binding, and any combinations thereof.

In one example, a detector (such as detector 110) is a separate component to an MIP. In one such example, a detector is brought into contact with an MIP after an MIP is exposed to a target item. The detector then can detect the presence of any target food allergen bound to one or more receptor sites of the MIP. In another such example, a detector is a color development agent and the color development agent is capable of being applied to an MIP of a food allergen detection platform after the MIP is exposed to a target item. The color development agent changes color based on the presence or absence of target food allergen bound to one or more of the receptor sites of the MIP.

In another example, a detector (such as detector 110) is directly associated with an MIP. In one such example, a detector is a component of a food allergen detection platform having an MIP. A directly associated detector can detect the presence of a target food allergen bound to one or more receptor sites of an MIP without having to bring the detector into contact with the MIP after the MIP is exposed to a target item. In one example using a color development agent, the color development agent may be a component of a food allergen detection platform along with an MIP. The color development agent has a direct change in color when a target food allergen is bound to one or more of the receptors of the MIP.

Alternative detectors to a visual indicator detector are also contemplated for use with an MIP of the current disclosure. Example alternative detectors include, but are not limited to, an electrical characteristic detector (e.g., a conductive detector, a capacitive detector). Combinations of such examples with a visual detector are also contemplated. An electrical characteristic detector is a detector that can determine changes in an electrical characteristic of an MIP based on the presence or absence of a target food allergen bound to one or more receptor sites of the MIP. Example electrical characteristics that can provide a basis for detecting the presence or absence of a target allergen include, but are not limited to, electrical resistance, electrical conductance, current, voltage, capacitance, transistor on current, transistor off current, transistor threshold voltage, and any combinations thereof. In an alternative example, a basis for detecting the presence or absence of a target food allergen may include a combination of properties, relationships between different properties, and/or a variation of one or more properties over time.

Capacitive detectors are well-known in the art and any suitable detector can be employed with an MIP of the current disclosure. In one example, a capacitive detector element can include a sandwich-type electrode configuration (e.g., with an MIP placed between two capacitor elements or electrodes). Any suitable conductor or semiconductor material can be used as an electrode. Example conductor/semiconductor materials include, but are not limited to, gold, platinum, silver, and any combinations thereof. In another example, an interdigitated capacitor device is combined with an MIP as part of a food allergen detection platform. The interdigitated capacitor device detects changes in capacitance of the MIP due to bound target food allergen. In one such example, a set of interdigitated electrodes with an MIP of the present disclosure coated onto the electrode assembly. In a specific example, a sandwich-type capacitive sensor is produced by depositing chromium on a glass, silicon, or mica substrate by thermal evaporation. The chromium is patterned by photolithography and treated, subsequently, by wet etching. An insulating silicon dioxide layer (e.g., with a thickness between 40 nm and 200 nm) is deposited onto the bottom electrode surface using an electron-gun thermal deposition technique. Subsequently, the MIP layer is spun coated on the substrate surface. A Cr film (e.g., with a thickness of 70 nm) is deposited on the MIP film surface by thermal evaporation, followed with patterning by photolighography and wet etching.

Any conductive detector can be used that will detect the presence and/or absence of a target food allergen. In one example, a conductive polymer is utilized with a template as a doping agent. In such an example, the presence or absence of a template molecule influences the conductivity of the polymer. Example conductive polymers include, but are not limited to, a it electron-conjugated conductive polymer, a polyaniline, a polyaniline derivative, a polypyrrole, a polypryrrole derivative, a polythiophene, a polythiophene derivative, a copolymer of two or more of the same, and any combinations thereof. In another example, a chemiresistor is combined with an MIP as part of a food allergen detection platform to detect changes in conductivity of an MIP due to the presence of a target food allergen bound to one or more receptor sites of the MIP. In one such example, a detection device (such as device 100) includes an electronic readout device connected to the interdigitated capacitor device and/or the chemiresistor for providing a user of the detection device with information regarding the change in capacitance/conductivity and/or information about the presence/quantitative amount of the target food allergen (e.g., via a comparison of data stored in a memory regarding a relation between the change in capacitance/conductivity and the presence/amount of the target food allergen).

A detector based on electrical characteristics may include and/or be associated with a power source. A power source can be electrically connected to a detector, a substrate, and/or an MIP for providing power to allow for detection of a target food allergen. In one example, a power source is included as a component of a food allergen detection platform. In another example, a power source is included in a detection device as a separate component to the food allergen detection platform. Examples of a power source include, but are not limited to, a battery, a solar cell, a fuel cell (e.g., a miniature and portable fuel cell), a thermocouple, a radio-frequency energy source, an electrochemical energy source, a supercapacitor, an energy scavenging device, and any combinations thereof. A power source may be used to power other components of a food allergen detection device.

A food allergen detection device (such as device 100) may include an electronic processing element (e.g., a microprocessor) for processing information and data related to the presence and/or absence of a target food allergen (e.g., where a detector of a food allergen detection device includes an electrical characteristic detector).

A food allergen detection device (such as device 100) may also include a memory element for storing information and data for assisting a processing element with determining the presence and/or absence of a target food allergen. Example memory elements include, but are not limited to, a magnetic disk (e.g., a conventional floppy disk, a hard drive disk), an optical disk (e.g., a compact disk "CD", such as a readable, writeable, and/or re-writable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combinations thereof. A memory may be included in a food allergen detection device as a part of a processing element, as a separate component to a processing element (e.g., with an electrical connection to the processing element), or both. In one example, a memory and a processing element are part of a food allergen detection platform. In another example, a memory and a processing element are a separate component of a food allergen detection device from a food allergen detection platform. A processing element may be electrically connected to a power supply, a memory element, a detector, an MIP (e.g., a substrate or other electrical characteristic portion of an MIP), another component of a food allergen detection device, and any combinations thereof. A memory may include any information and data that may be utilized by a processing element in determining a presence and/or absence of a food allergen. Example information includes, but is not limited to, information on an MIP material, information on an MIP layer thickness, information of a conductive detector element material, information of a conductive detector element thickness, information of a capacitive detector element material, information of a capacitive detector element thickness, information of an electrical characteristic detector, information of a target food allergen (e.g., resistance, conductive, capacitive properties of a target food allergen), machine readable instructions for determining a presence and/or absence of a target food allergen, machine readable instructions for executing any one or more of the embodiments and/or implementations described in the current disclosure, and any combinations thereof.

A food allergen detection device (e.g., device 100) may also include a user input element. A user input element is an electronic and/or mechanical component allowing a user to provide an input to a food allergen detection device (e.g., providing an input to a processing element of a food allergen detection device). A user input element may be electrically and/or mechanically connected to a component of a food allergen detection device. In one example, a user input element is electrically and/or mechanically connected to a processing element of a food allergen detection device. Examples of an input element include, but are not limited to, a button, a toggle, an alpha-numeric input device (e.g., a keyboard), a pointing device, a joystick, an audio input device (e.g., a microphone, a voice response system, etc.), a cursor control device (e.g., a mouse), a touchpad, a video capture device (e.g., a still camera, a video camera), touch screen, and any combinations thereof. Example uses for an input element include, but are not limited to, allowing a user to start a process of detecting the presence or absence of a food allergen, allowing a user to stop a process of detecting the presence or absence of a food allergen, and any combinations thereof.

A food allergen detection device (e.g., device 100) may also include an output element. An output element is an electronic, chemical, and/or mechanical component providing an indication of a result of a detecting by a food allergen detection device of a presence and/or absence of a food allergen. An output element may, in some examples, indicate an amount of a food allergen present (e.g., a quantitative value of food allergen present). An output element may be electrically and/or mechanically connected to components of a food allergen detection device. In one example, an output element is electrically connected to a processing element of a food allergen detection device. Examples of an output element include, but are not limited to, a display element (e.g., an LCD screen, an LED screen), a chemical change visual indicator, a light element (e.g., a LED light indicating a presence or absence of a food allergen), and any combinations thereof.

Figure 4:
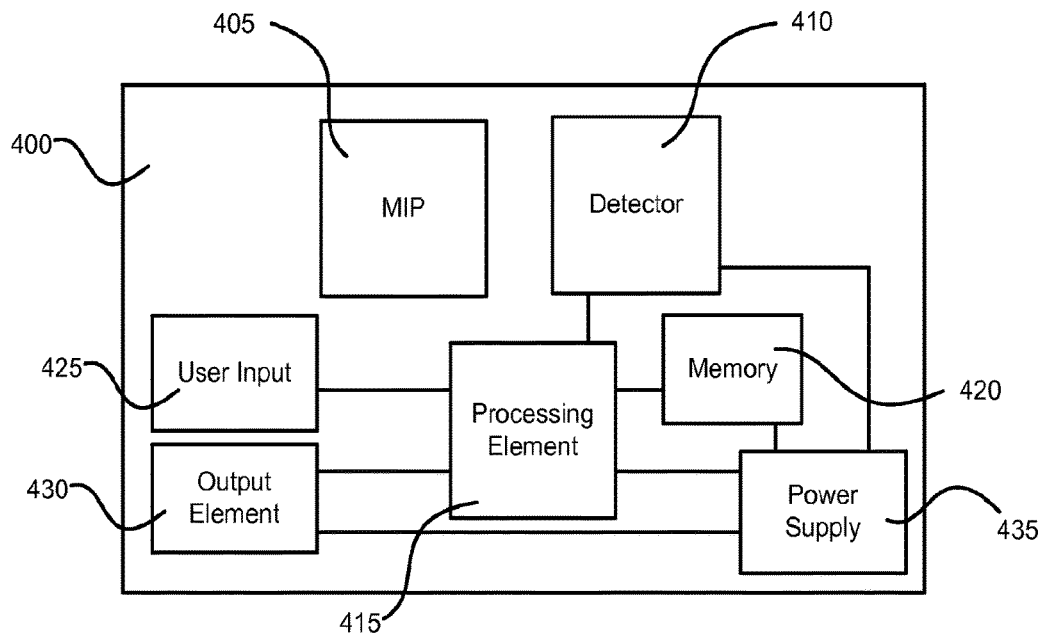
FIG. 4 illustrates another exemplary implementation of a food allergen detection device.

FIG. 4 illustrates another implementation of a food allergen detection device 400. Food allergen detection device includes components for which exemplary aspects and features are discussed throughout the current disclosure (e.g., with respect to device 100 of FIG. 1). Except as indicated these exemplary aspects and features may be applied to components of device 400. Device 400 includes an MIP 405 and a detector 410. Device 400 also includes a processing element 415 connected to detector 410 (e.g., for processing data and information related to the presence or absence of a target food allergen bound to MIP 405). Processing element 415 may also be connected to MIP 405 (e.g., where MIP 405 includes as a component thereof detector 410 or a portion of detector 410). Device 400 also includes a memory 420 (connected to processor 415), a user input element 425 (connected to processor 415), and an output element 430 (connected to processor 415). Processor 415 may be configured to control input element 425 and output element 430 (e.g., using machine executable instructions and/or other information stored in memory 420. Device 400 also includes a power supply 435 connected to processing element 415, memory 420, user input 425, output element 430, and detector 410. Power supply 435 may also be connected to other components that may require power (e.g., user input 425 if user input 425 includes an electrical component). In other examples, power supply 435 may be connected to fewer components (e.g., where a component does not require power, such as a detector that is a chemical visual indicator detector.

A food allergen detection device may include one or more MIPs that are imprinted (i.e., have receptor sites) to two or more target allergens. In one example, an MIP is imprinted for two or more target allergens. In another example, a food allergen detection device includes a plurality of MIP's with at least two of the MIPs imprinted for different target allergens. In one such example, the plurality of MIP's are in an array. One or more MIP's that are imprinted to two or more target allergens may be a component of a food allergen detection platform as discussed herein. An MIP imprinted for a food allergen, a food allergen detection platform having an MIP imprinted for a food allergen, and/or a detector may be removable from a detection device. In one such aspect, a detection device includes a holder in which an MIP, a food allergen detection platform, and/or a detector may be removed from the holder.

Figure 5:
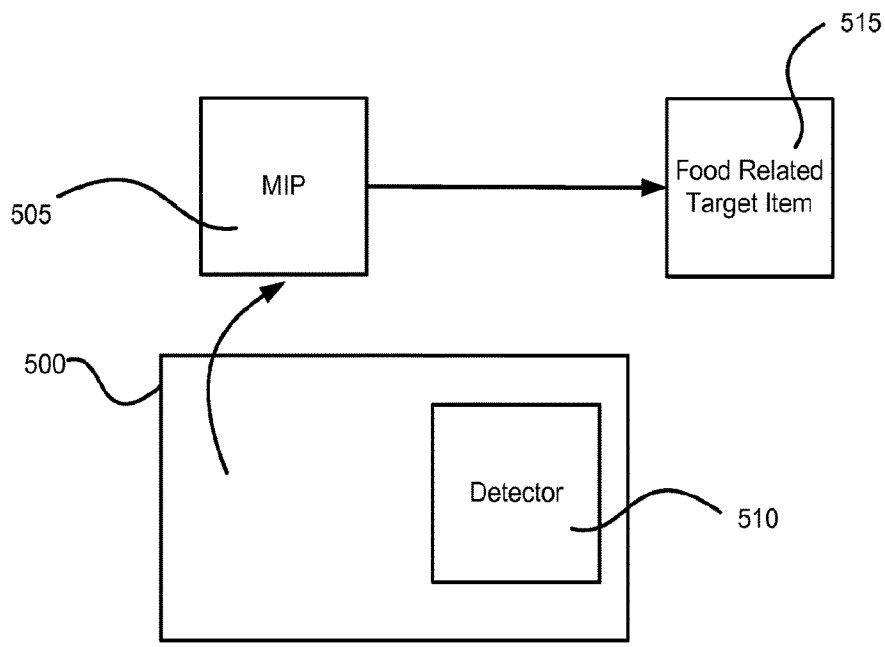
FIG. 5 illustrates yet another exemplary implementation of a food allergen detection device.

FIG. 5 illustrates one example of a food allergen detection device 500 including an MIP 505 that is removable from device 500 (e.g., from a holder of device 500). MIP 500 is shown as being removed from device 500. MIP 505 may be a part of a food allergen detection platform that is removable from device 500. MIP 505 is shown as being contactable with a food related target item 515. Device 500 includes a detector 510 for detecting the presence of a target food allergen bound to one or more of the receptor sites of MIP 505. Example detectors and aspects thereof are discussed above and are applicable to device 500. In one example, MIP 505 is reinserted to device 500 after exposure to target item 515 and brought into contact with detector 510 to allow detector 510 to detect a target food allergen bound to one or more receptor sites of MIP 505. In one such example, MIP 505 (as part of a food allergen detection platform that is in a form of a dipstick/test stick) is insertable into an opening in device 500 exposing MIP 505 to detector 510 (e.g., a color development agent in liquid form). In another example, detector 510 is also removable from device 500 and is configured to be contactable with MIP 505 after exposure to target item 515 to allow detector 510 to detect a target food allergen bound to one or more receptor sites of MIP 505. In one such example, detector 510 includes a color development agent that can be applied to MIP 505 externally to device 500. In still another example, detector 510 and MIP 505 are both components of a food allergen detection platform that is removable from device 500 such that after MIP 505 is exposed to target item 515, detector 510 is already in contact with MIP 505 to detect a target food allergen bound to one or more receptor sites of MIP 505. Food allergen detection device 500 may also include one or more other components of a detection device as disclosed herein (e.g., with respect to device 100 and/or device 400).

A food allergen detection device according to any of the implementations, embodiments, and/or examples described herein may be portable. A food allergen detection device according to any of the implementations, embodiments, and/or examples described herein may be designed and configured for use at the point of consumption of a food item by a user. Example aspects discussed herein that may, in certain examples, assist in the use at a point of consumption include, but are not limited to, a portability of a device, a wearability of a device, a removability of an MIP from a device, other aspects and configurations described herein, and any combinations thereof.

A food allergen detection device according to any of the implementations described herein may be integrated into an article wearable by a human. Example articles wearable by a human include, but are not limited to, a jewelry article, a badge, and any combinations thereof. In one example, an article wearable by a human is an article of jewelry. Example articles of jewelry include, but are not limited to, a necklace, a bracelet, an amulet, a locket, and any combinations thereof.

A food allergen detection device according to any of the implementation described herein (e.g., a portable device, a wearable device, etc.) may include a visual symbol element of the target food allergen for which the device is configured to detect. For example, a visual symbol element for a device that targets peanut allergens can be a visual symbol element depicting a peanut, a visual symbol element for a device that targets milk and/or other dairy allergens can be a visual symbol element depicting a cow, a visual symbol element for a device that targets egg allergens can be a visual symbol element depicting an egg, a visual symbol element for a device that targets gluten and/or wheat allergens can be a visual symbol element depicting a sheaf of wheat, etc. Example visual symbol element forms include, but are not limited to, a charm affixed to a device, an etching in a surface of a device, the shape of a device or a portion of a device itself, another structural visual depiction of a target food allergen, and any combinations thereof. A device may include multiple visual symbol elements (e.g., where the device targets more than one food allergen). A visual symbol element may be removable. In one exemplary aspect, a visual symbol element of a target food allergen may be helpful for individuals in recognizing the type of allergen an individual is sensitive to, such as when the individual cannot explain the allergy themselves. For example, a waitress may recognize that a patron is allergic to peanuts upon seeing a peanut charm on a device worn by the patron. The waitress may deter the individual from eating certain dishes and/or provide appropriate action if the patron is having an allergic reaction.

A food allergen detection device may include an anti-allergen component. Example anti-allergen components include, but are not limited to, an Epi-Pen (e.g., a small sized Epi-Pen), epinephrine, an antihistamine, and any combinations thereof. An anti-allergen component may be integrated directly into the device. In another example, an anti-allergen component is associated with the device (e.g., as a kit). An anti-allergen component may also be removable. In one exemplary aspect, an anti-allergen component is configured to allow a user of the device to apply the anti-allergen component to an individual having an allergic reaction (e.g., an allergic reaction to an allergen detected by the device) and/or an individual as a precautionary measure based on detecting the presence of an allergen detected by the device. Exemplary forms for an anti-allergen component for administration to an individual include, but are not limited to, a pill form, an injection form, a liquid form, and any combinations thereof.

Benefits that may be part of a food allergen detection device of one or more of the implementations described herein include, but are not limited to, a high sensitivity to detecting certain food allergens, a high selectivity of detecting certain food allergens (e.g., using a portion of a food allergen to surface imprint an MIP), portable and small form, ease of use by a consumer (e.g., devices lacking electronics may not require power, devices with electronic detectors requiring minimal power suitable for battery operation), mobility, wearability, long shelf-life (e.g., water insoluble polymers can provide long shelf lives), low cost, ability to use at the point of consumption of an allergen-containing substance, and any combinations thereof.

Figure 6:
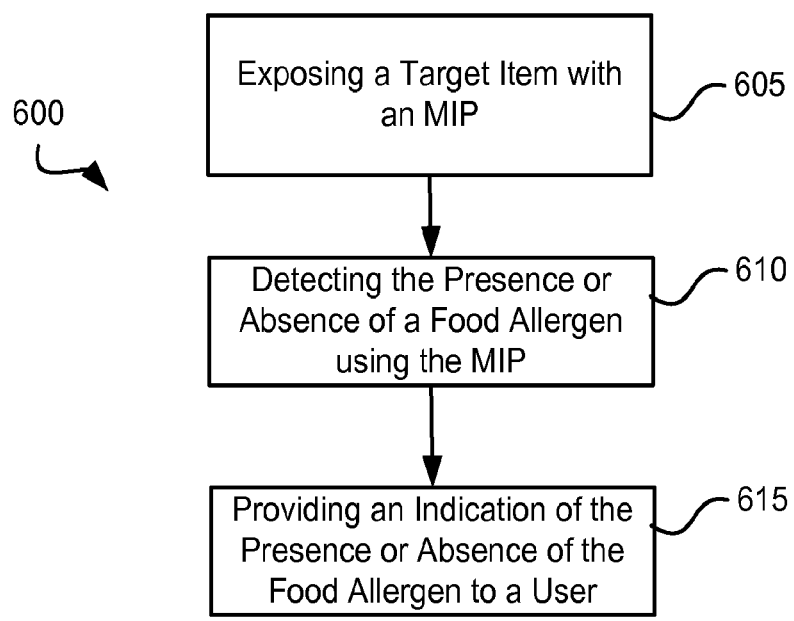
FIG. 6 illustrates an exemplary implementation of a method for detecting a food allergen using an MIP.

FIG. 6 illustrates an exemplary method 600 for detecting a food allergen using an MIP of the current disclosure. At step 605, a target item is exposed to an MIP encoded to detect a target food allergen. The MIP may be a component of a food allergen detection platform. Aspects and features of an MIP and a food allergen detection platform are discussed above. Some of the aspects and features are discussed in detail again with respect to method 600, but other aspects and features are also applicable to method 600 as appropriate. In one example, a food allergen detection platform includes a substrate and an MIP layer that includes a polymer imprinted with receptor sites created by a template. An MIP may be surface imprinted. A food allergen detection platform may also include a visual indicator (e.g., a color development agent). In another example, an MIP may be associated with an electrical characteristic detector. Exposing a target item to an MIP may occur in a variety of ways. Example ways to expose a target item to an MIP include, but are not limited to, direct contact of an MIP to a target item, applying a target item (e.g., a sample of a target item) to an MIP (e.g., via a liquid dropper, via an applicator configured to transfer a solid or semisolid target item to an MIP, etc.), removal of an MIP from a holder of an allergen detection device to put the MIP in contact with a target item, removal of an MIP from a holder of an allergen detection device to apply a target item to the MIP, and any combinations thereof.

At step 610, the presence or absence of a target food allergen is detected. Detection of the presence or absence of a target food allergen may occur in a variety of ways. In one exemplary aspect, detection of the presence or absence of a target food allergen may be performed by detecting the presence or absence of one or more molecules of an indicator of the food allergen being bound to one or more receptor sites of the MIP. An MIP may be a component of an food allergen detection platform as discussed herein. Detection may include determining an amount of the food allergen present (e.g., not just determining the presence or lack of presence). In another example, the mere presence or absence may be detected without determining an amount.

Example ways to detect the presence or absence of a target food allergen include, but are not limited to, detecting an electrical characteristic of an MIP or a material associated with the MIP (e.g., a substrate), detecting a chemical interaction that produces a color change in the presence of a target food allergen, detecting a lack of a chemical interaction that produces a color change in the absence of a target food allergen, detecting presence or absence of a target food allergen using another visual-type indicator, and any combinations thereof. The various features, embodiments, implementation, and examples of detectors and their processes discussed above are applicable here to the detection of the presence or absence of a target food allergen. For example, detecting an electrical characteristic may include detecting electrical resistance, electrical conductance, current, voltage, capacitance, transistor on current, transistor off current, and/or transistor threshold voltage. Example electrical characteristic detector elements and their features are described in detail above. Detection of an electrical characteristic may occur via detection of a signal (e.g., using a processing element or other circuitry, examples of which are described above).

In one example of detecting a visual indication (e.g., a color change or lack thereof), a color development agent is applied to an MIP to produce a detectable color change in the presence of a target food allergen. Exemplary ways of application of a color development agent (or other chemical additive that produces a visual change or other detectable event) include, but are not limited to, applying a liquid agent to an MIP (e.g., using a liquid dropper device), having an agent be in contact with an MIP (e.g., as a component of a food allergen detection platform, as an integral component of an MIP) prior to the exposing step 605, bringing an agent into contact with an MIP outside of a holder of a food allergen detection device, bringing an agent into contact with an MIP internally to a holder of a food allergen detection device, and any combinations thereof. Examples of color development agents and their features are discussed above.

Method 600 may include a step (not shown) of rinsing an MIP (e.g., by rinsing a food allergen detection platform having an MIP). In one example, a rinsing step occurs after the exposing step 605 and prior to (or at about the same time as) detecting step 610. One potential benefit to rinsing may be to remove materials that are not bound to a receptor site. Such materials may interfere with the detecting step (e.g., provide false positive measurements, impact quantitative measurement, etc.).

At step 615, a result indication of the presence of the target food allergen is provided to a user. In one example, the indication is generated by a visual indicator detector that performs the detecting of the binding and the indication to the user. In one such example, a visual indicator is a color development agent. The provision of a result indication of the presence of a target food allergen may occur as a component of the detecting step 610. For example, when a visual indicator detector is used the detection may involve a color change in a chemical agent, the color change providing a visual indication to the user. In another example, an electronic display or other output device may be utilized to provide information and/or data related to the detection (e.g., an electronic indication of the presence or absence, a quantitative indication, etc.).

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed:

1. A device comprising:
   a food allergen detection platform comprising:
      a substrate; and
      a molecularly imprinted polymer layer in contact with the substrate, the molecularly imprinted polymer layer comprising receptor sites imprinted in a first surface of the polymer, the receptor sites configured to accept a first indicator of a first food allergen, and the receptor sites having been formed with a first template molecule; and
      a detector comprising an electrical characteristic detector integrated into the substrate and/or the molecularly imprinted polymer, and which is configured to detect the presence of the first food allergen upon binding of one or more molecules of the first indicator to one or more of the receptor sites;
   wherein:
      the device is a food allergen detection device;
      the first template molecule is a molecule of the first food allergen, or a portion thereof which is indicative of the first food allergen; and
      the molecule of the first food allergen is a protein, a portion of a protein, or an epitope of a protein.

2. The device of claim 1, wherein the molecule of the first food allergen is a protein.

3. The device of claim 1, wherein a portion of the molecule of the first food allergen is a portion of a protein.

4. The device of claim 1, wherein the molecule of the first food allergen is an epitope of a protein.

5. The device of claim 1, wherein the molecule of the first food allergen is a 14-peptide epitope, DLAFPGSGEQVEKL.

6. The device of claim 1, wherein the first food allergen comprises a peanut allergen, a tree nut allergen, a fish allergen, a dairy allergen, a fruit allergen, a legume allergen, a grain allergen, a beverage allergen, a chocolate allergen, a synthetic chemical allergen found in food, or a combination of any two or more thereof.

7. The device of claim 1, wherein the first food allergen comprises a peanut allergen.

8. The device of claim 1, wherein the polymer comprises a poly(4-vinylphenol), a poly(urethane), a poly(methylmethacrylate), a poly(methacrylic acid), poly(hydroxyethylmethacrylate), poly(vinylpyrrolidone), a co-polymer of any two or more there, or a polymer blend of any two or more thereof.

9. The device of claim 1, wherein the first indicator is a food protein.

10. The device of claim 1, wherein the first indicator is a peanut food protein.

11. The device of claim 1, wherein the first indicator is *arachis hypogaea* allergen 1 (ara h1), *arachis hypogaea* allergen 2 (ara h2), *arachis hypogaea* allergen 3 (ara li3), or a combination of any two or more thereof.

12. The device of claim 1, wherein the substrate comprises a glass, a plastic, a paper, a quartz, alumina, mica, silicon, a III-IV semiconductor compound, or a combination of any two or more thereof.

13. The device of claim 1, wherein the electrical characteristic detector is a thermistor, an integrated circuit element, or a combination thereof.

14. The device of claim 1, wherein the electrical characteristic detector is an electrical resistance detector, electrical conductance detector, a current detector, a voltage detector, a capacitance detector, a transistor on current detector, a transistor off current detector, a transistor threshold voltage detector, or a combination of any two or more thereof.

15. A method for detecting a food allergen, the method comprising:
   exposing a first target item with a food allergen detection platform, the detection platform comprising:
      a substrate; and
      a molecularly imprinted polymer layer in contact with the substrate, the molecularly imprinted polymer layer comprising a polymer imprinted on a first surface of the polymer with receptor sites created by a first template, the receptor sites configured to detect a first indicator of a first food allergen;
   detecting the presence or absence of one or more molecules of the first indicator bound to one or more of the receptor sites by detecting an electrical characteristic of the molecularly imprinted polymer layer and/or the substrate; and
   providing an indication of the presence of the first food allergen;
   wherein:
      the first template is a molecule of the first food allergen, or a portion thereof which is indicative of the first food allergen; and
      the molecule of the first food allergen is a protein, a portion of a protein, or an epitope of a protein.

16. The method of claim 15, wherein the electrical characteristic is an electrical characteristic selected from the group consisting of an electrical resistance, an electrical conductance, a current, a voltage, a capacitance, a transistor on current, a transistor off current, a transistor threshold voltage, and any combinations thereof.

* * * * *